United States Patent
Harada et al.

(10) Patent No.: US 9,638,627 B2
(45) Date of Patent: May 2, 2017

(54) INTEGRATING SPHERE

(71) Applicant: HONDA MOTOR CO., LTD., Tokyo (JP)

(72) Inventors: Hironori Harada, Wako (JP); Kenji Matsumoto, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 234 days.

(21) Appl. No.: 14/294,516

(22) Filed: Jun. 3, 2014

(65) Prior Publication Data

US 2014/0362380 A1 Dec. 11, 2014

(30) Foreign Application Priority Data

Jun. 7, 2013 (JP) ................................. 2013-120693
Mar. 13, 2014 (JP) ................................. 2014-049969

(51) Int. Cl.
| | | |
|---|---|---|
| *G01J 3/46* | (2006.01) | |
| *G01N 21/25* | (2006.01) | |
| *G01J 1/08* | (2006.01) | |
| *G01J 3/50* | (2006.01) | |

(52) U.S. Cl.
CPC .............. *G01N 21/255* (2013.01); *G01J 1/08* (2013.01); *G01J 3/501* (2013.01); *G01N 21/251* (2013.01)

(58) Field of Classification Search
CPC ....... G01N 21/255; G01N 21/251; G01J 1/08; G01J 3/501
See application file for complete search history.

(56) References Cited

U.S. PATENT DOCUMENTS

| | | | | | |
|---|---|---|---|---|---|
| 4,583,860 | A | * | 4/1986 | Butner ................. | G01N 21/255 250/228 |
| 4,768,182 | A | * | 8/1988 | Hatfield ................ | G01B 11/06 356/497 |
| 5,519,534 | A | * | 5/1996 | Smith .................... | A61N 5/062 250/228 |
| 6,583,879 | B1 | * | 6/2003 | Berg ........................ | G01J 3/02 250/226 |

(Continued)

FOREIGN PATENT DOCUMENTS

JP 4272629 B2 6/2009

OTHER PUBLICATIONS

Isokinetics, Inc. (https://web.archive.org/web/20120307060255/http://www.isokineticsinc.com/product/bbblk) Mar. 7, 2012.*

*Primary Examiner* — Hina F Ayub
(74) *Attorney, Agent, or Firm* — Squire Patton Boggs (US) LLP (57) ABSTRACT

In an integrating sphere including a structure having a spherical inner wall that forms a spherical space, there are provided an LED circuit board equipped at one end with a light-emitting device adapted to radiate a light in the space at an input port formed at the structure to be diffuse-reflected on the spherical inner wall and equipped at other end with a heat sink, a measuring port formed at the structure to pass the light diffuse-reflected on the spherical inner wall on a measuring object, an output port formed at the structure to output a reflected light of the diffuse-reflected light passing the measuring port and reflected on the measuring object outside, and a detector adapted to be detachably connected to the output port to receive the outputted reflected light.

11 Claims, 7 Drawing Sheets

(56) References Cited

U.S. PATENT DOCUMENTS

| | | | | |
|---|---|---|---|---|
| 2004/0000015 A1* | 1/2004 | Grossinger | .......... | A45D 44/005 |
| | | | | 8/405 |
| 2005/0134853 A1* | 6/2005 | Ingleson | ............... | G01J 3/0251 |
| | | | | 356/402 |
| 2005/0194516 A1* | 9/2005 | Littleton | .................. | G01J 1/08 |
| | | | | 250/205 |
| 2006/0198761 A1* | 9/2006 | Tokhtuev | ............. | G01N 21/251 |
| | | | | 422/82.05 |
| 2011/0027818 A1* | 2/2011 | Frederickson | ....... | G01N 21/643 |
| | | | | 435/29 |
| 2011/0067489 A1* | 3/2011 | Haberstroh | ......... | B01L 3/50857 |
| | | | | 73/64.56 |
| 2011/0305599 A1* | 12/2011 | Tan | ........................ | G01N 21/45 |
| | | | | 422/69 |
| 2013/0271764 A1* | 10/2013 | Margraf | ................ | G01J 3/0254 |
| | | | | 356/402 |
| 2014/0248693 A1* | 9/2014 | Maher | ................ | G01N 21/6452 |
| | | | | 435/287.2 |
| 2016/0046820 A1* | 2/2016 | He | ........................ | H04L 67/125 |
| | | | | 709/203 |

\* cited by examiner

INTEGRATING SPHERE

BACKGROUND

Technical Field

This invention generally relates to an integrating sphere, more particularly to a structure thereof.

Related Art

An integrating sphere used in analysis of luminous flux of a light source or color of a measuring object is generally provided with a structure having a spherical inner wall (surface) wherein a light radiated from the light source repeats diffuse reflection on the spherical inner wall to be spatially-integrated, for example, as disclosed in Japanese Patent No. 4,272,629.

Specifically, in a conventional integrating sphere other than that disclosed in the reference, binders have been used to enhance release strength of a white coating material, as the release strength of the white coating material is significantly low in powder foam. Nevertheless, the release strength of the white coating material is still insufficient even using binders and what is worse, binders can be discolored by heat or ultraviolet light. Taking this into account, in the sphere disclosed in the reference, the spherical surface is configured to be coated, not with binders, but with a spraying membrane having a diffuse reflectivity for an incident light in the wavelength region to be used.

SUMMARY

Integrating spheres, including that disclosed in the reference, generally use a strong infrared radiation lamp such as a tungsten lamp or halogen lamp, as a light source. With this, a measuring object is heated instantaneously by strong incident infrared light. Therefore, if a measuring object is susceptible to heat like an organic material, it can be discolored during measurement, rendering it difficult to measure the color of the object accurately.

As taught by the reference, degradation of the spherical inner wall can be avoided to some extent with the use of the spraying membrane. However, the spherical inner wall is still susceptible to be degraded by infrared light radiated from the light source or heat from the infrared light or light source. Disadvantageously, spraying requires large facilities.

Therefore, embodiments of this invention are aimed to overcome the foregoing problems by providing an integrating sphere that measures a color of a measuring object with a light radiated from a light source and diffuse-reflected on a spherical inner wall of a structure, while suppressing deterioration of the spherical inner wall or degradation of measurement accuracy by reducing a thermal load.

In order to achieve the object, embodiments of this invention provide an integrating sphere including a structure having a spherical inner wall that forms a spherical space, comprising: an LED circuit board equipped at one end with a light-emitting device adapted to radiate a light in the space at an input port formed at the structure to be diffuse-reflected on the spherical inner wall and equipped at other end with a heat sink; a measuring port formed at the structure to pass the light diffuse-reflected on the spherical inner wall on a measuring object; an output port formed at the structure to output a reflected light of the diffuse-reflected light passing the measuring port and reflected on the measuring object outside; and a detector adapted to be detachably connected to the output port to receive the outputted reflected light.

BRIEF DESCRIPTION OF THE DRAWINGS

The above and other objects and advantages of embodiments of this invention will be more apparent from the following description and drawings in which.

DESCRIPTION OF EMBODIMENTS

First Embodiment

An integrating sphere according to a first embodiment of this invention will now be explained with reference to the attached drawings.

Figure 1:
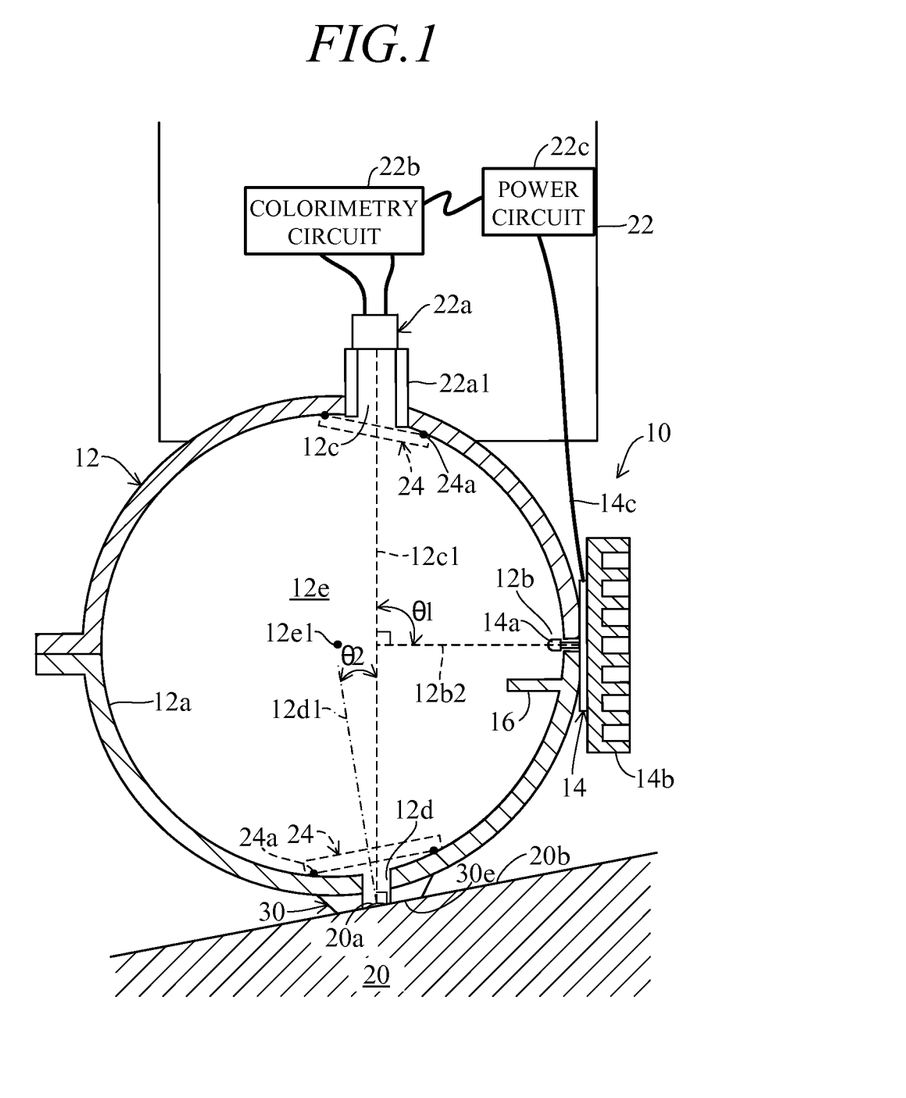
FIG. 1 is an overall schematic view of an integrating sphere according to a first embodiment of this invention.

FIG. 1 is an overall schematic view of the integrating sphere according to the first embodiment of this invention.

In FIG. 1, symbol 10 indicates an integrating sphere. The integrating sphere 10 includes a structure 12 of a spherical shape as shown. The structure 12 has a spherical inner wall (surface) 12a coated with a diffuse reflective coating and spherically-curved with a predetermined curvature, and is formed with an input (incident) port 12b, an output (emission) port 12c and a measuring (detector) port 12d thereat.

The inner wall 12a of the structure 12 is applied with diffuse reflective coating by a known technique so as to allow a light to be diffuse-reflected on the wall (surface) 12a. The inner wall 12a forms a spherical space 12e in the structure 12.

The structure 12 is equipped with an LED circuit board 14. The LED circuit board 14 is connected, at one end (the side close to the structure 12), with a light-emitting device (light source; schematically shown in FIG. 1) 14a and is equipped, at the other end (the side remote from the structure 12), with a heat sink (radiation fin) 14b for radiating heat. Thus, the LED circuit board 14 is connected to the input port 12b at a location outside of the structure 12.

The light-emitting device comprises an LED (light-emitting diode), and adapted to radiate a light in the spherical space 12e at the input port 12b to be diffuse-reflected on the spherical inner wall 12a, i.e., adapted to be inserted into the spherical space 12e at the input port 12b to radiate the light (white light) to be diffuse-reflected on the spherical inner wall 12a.

As known, there is a tendency that an amount of heat generated by the LED is smaller than that of the light bulb or fluorescent light and remains at a relatively low level even when it has been used for a long time. Advantageously, almost the entire emission component of white LED is in the visible region.

In the structure 12, a baffle (shading plate) 16 is provided in the vicinity of the light-emitting device 14a. The baffle 16 is made of a low thermal conductive material (heat insulator), for example, Teflon (R).

In the integrating sphere 10, the incident light radiated from the light-emitting device 14a at the input port 12b is repeatedly diffuse-reflected on the inner wall 12a to be spatially-integrated. Specifically, in the spherical space 12e formed with the inner wall 12a of the structure 12, the intensity of the incident light is uniformly distributed in proportion to the light intensity of the light-emitting device 14a, irrespectively of spread of the light of the light of the light-emitting device 14a or incident angle of the light of the device 14a.

The structure 12 is configured to have the measuring port 12d formed thereat to pass the light diffuse-reflected on the spherical inner wall 12a on a measuring object 20, more specifically a portion (local portion) 20a of the object 20, and the output port 12c formed at the structure 12 to output the reflected light of the diffuse-reflected light passing the measuring port 12d and reflected on the measuring object 20 outside. The portion 20a of the object 20 is exaggerated in FIG. 1. Hereinafter, the measuring object 20 is renumbered as "20a".

When the light of the light-emitting device 14a is radiated from the input port 12b into the spherical space 12e formed with the inner wall 12a of the structure 12, the incident angle of the light is restricted by the baffle 16 and the light of the light-emitting device 14a may not directly radiate to (incident on) the measuring object 20a.

Outside the structure 12, a detector (measuring instrument) 22 is detachably connected to the output port 12c. The detector 22 has a sensor 22a made of a RGB phototransistor of a tristimulus-value direct reading type, a colorimetry circuit 22b that is constituted by a microcomputer and measures (analyzes) a color(s) of the measuring object 20a based on an output of the sensor 22a, a power circuit (battery) 22c and a liquid crystal display (not shown).

The LED circuit board 14 is connected to the power circuit 22c through a cable 14c. When a direct current is supplied from the power circuit 22c, the LED circuit board 14 actuates the light-emitting device 14a to emit the light.

The detector 22 has a tubular duct (light-absorbing portion) 22a1 formed at a position facing the output port 12c, and an inner wall of the tubular duct 22a1 is painted black to prevent direct incident of the light and the like by absorbing them. The sensor 22a is placed inside, i.e., at an inner location of the tubular duct 22a1.

Thus, the integrating sphere 10 comprises the structure 12 and the detector 22 detachably attached thereto. The detector 22 accommodates the power circuit 22c and liquid crystal display and has a grip (not shown) at its end such that the operator can grasp the grip and carry the integrating sphere 10 to carry out measurement operation.

As shown, in the structure 12, the output port 12c and the measuring port 12d are closed with windows 24 (indicated by dashed line) at the inside. The windows 24 are made of transparent materials to the visible light such as synthetic quarts and allow the diffuse-reflected light to pass therethrough. The windows 24 are air-tightly and liquid-tightly attached to the inner wall 12a of the structure 12 by O-rings 24a provided along the edge of the output port 12c and measuring port 12d.

With this, the windows 24 are configured to be water-proof and air-proof so that the spherical space 12e formed by the inner wall 12a of the structure 12 is closed up tightly to prevent entry of foreign materials including water vapor and oil vapor from outside.

As shown in the figure, in the structure 12, the input port 12b, the output port 12c and the measuring port 12d are formed in the spherical space 12e in such a manner that a crossing angle $\theta 1$ of a central axis line 12b2 of the input port 12b and a central axis line 12c1 of the output port 12c is 90 degrees (i.e., is exactly or approximately 90 degrees) and a crossing angle $\theta 2$ of the central axis line 12c1 of the output port 12c and a normal line 12d1 extending from a measuring surface 20b (on which the measuring object 20a is held) towards the spherical space 12e through the center of the measuring port 12d is an angle within a predetermined range, more precisely an angle greater than 0 degree, but equal to or smaller than 10 degrees.

To be more specific, the integrating sphere 10 is configured such that a measuring guide 30 is detachably attached to the structure 12 in the vicinity of the measuring port 12d from outside of the measuring port 12d to hold the measuring object 20a on the measurement surface 20b, more specifically to hold it with the crossing angle $\theta 2$ of the central axis line 12c1 of the output port 12c and the normal line 12d1 extending from the measurement surface 20b within the predetermined range. The measuring guide 30 is of an approximately inverse truncated cone shape and has a flat surface 30e that can abut on the measurement surface 20b.

The measuring port 12d is formed in the structure 12 such that the normal line 12d1 extends through a center point 12e1 of the spherical space 12e, in other words, the measuring surface 20b (holding the measuring object 20a through the guide 30) faces the center point 12e1 of the spherical space 12e in the measuring port 20d. In addition, the input port 12b is also formed in the structure 12 such that its central axis line 12b2 passes through the center point 12e1 of the spherical space 12e.

As mentioned above, in the integrating sphere 10 according to the embodiment, since the structure 12 of the sphere 10 is configured to have the measuring port 12d formed at the structure 12 to pass the light diffuse-reflected on the spherical inner wall 12a on the measuring object 20a, and the output port 12c formed at the structure 12 to output the reflected light of the diffuse-reflected light passing the measuring port 12d and reflected on the measuring object 20a outside. With this, it becomes possible to make the diffuse-reflected light of uniform intensity reflect on the measuring object 20a and to measure or analyze the color of the measuring object 20a accurately, even when the measuring object 20a is an object that can be affected by an angle at which the measurement is conducted.

Further, since the LED circuit board 14 is equipped with the heat sink 14b at the other end, it becomes possible to eliminate heat generated by the LED circuit board 14 by the heat sink 14b and to prevent heat from diffusing into the structure 12.

Further, since the LED light-emitting device 14a is used as the light source for light radiation, it becomes possible to suppress deterioration of the spherical inner wall 12a, and since the amount of heat generated by the LED light-emitting device 14a is relatively small, it becomes possible to suppress deterioration of the spherical inner wall 12a due to heat emitted from the light-emitting device 14a, thereby enabling to enhance durability.

Since the LED circuit board 14 is placed at a location outside of the structure 12, it becomes possible to suppress deterioration of the spherical inner wall 12a coated with diffuse reflection coating more effectively.

Since the input port 12b, the output port 12c and the measuring port 12d are formed in the spherical space 12e in such a manner that the crossing angle θ1 of the central axis line 12b2 of the input port 12b and the central axis line 12c1 of the output port 12c is made 90 degrees and the crossing angle θ2 of the central axis line 12c1 of the output port 12c and a normal line 12d1 extending from a measuring surface 20b (on which the measuring object 20a is held) towards the spherical space 12e through the center of the measuring port 12d is made an angle within a predetermined range, i.e., an angle greater than 0 degree and equal to or smaller than 10 degrees, it becomes possible to make the fabrication of the structure 12 easier.

Explaining this, since the structure 12 needs to be formed with fixing or attaching portions for fixing or attaching the LED circuit board 14 (or light-emitting device 14a) or the detector 22 at the input port 12b and output port 12c, it is inherently tedious to fabricate the structure 12. However, since the crossing angle θ1 of the central axis line 12b2 of the input port 12b and the central axis line 12c1 of the output port 12c is made 90 degrees, i.e., is made exactly or absolutely 90 degrees, it becomes possible to simplify the configuration of the structure 12 and to facilitate the fabrication.

Aside from the fabrication, since the crossing angle θ2 of the central axis line 12c1 of the output port 12c and the normal line 12d1 extending from the measuring surface 20b (on which the measuring object 20a is held) towards the spherical space 12e through the center of the measuring port 12d is made an angle within a predetermined range, for example an angle greater than 0 degree and equal to or smaller than 10 degrees, it becomes possible to prevent the light reflected from the measuring object 20a from entering the detector 22 at a regular reflection angle (angle at which the reflection angle becomes equal to the incident angle), thereby enabling to enhance measurement accuracy.

Further, since the crossing angle θ2 of the central axis line 12c1 of the output port 12c and the normal line 12d1 extending from the measuring surface 20b (on which the measuring object 20a is held) towards the spherical space 12e through the center of the measuring port 12d is made an angle within a predetermined range, it becomes possible to make the size of the baffle 16 (for preventing direct incident from the light-emitting device 14a to the measuring object 20a) smaller.

Furthermore, since the measuring port 12d is formed at the structure 12 in such a manner that the normal line 12d1 extends through the center point 12e1 of the spherical space 12e, it becomes possible to allow the light radiated from the light-emitting device 14a and diffuse-reflected on the spherical inner wall 12a to uniformly enter and uniformly reflected on the measuring object 20a, thereby enabling to enhance measurement accuracy.

Since the detector 22 is detachably attached to the output port 12c through the duct 22a1, it becomes possible to effectively prevent light incident other than from the measuring object 20a, thereby enabling to enhance measurement accuracy.

Since the integrating sphere is configured such that, the output port 12c and the measuring port 12d are closed with the windows 24 that allow the diffuse-reflected light to pass therethrough, it becomes possible to prevent entry of foreign materials including water or oil vapor into the structure 12, thereby enabling to suppress deterioration or discoloration of the spherical inner wall 12a.

Second Embodiment

Next, an integrating sphere according to a second embodiment of this invention will now be explained with reference to the attached drawings.

Figure 2:
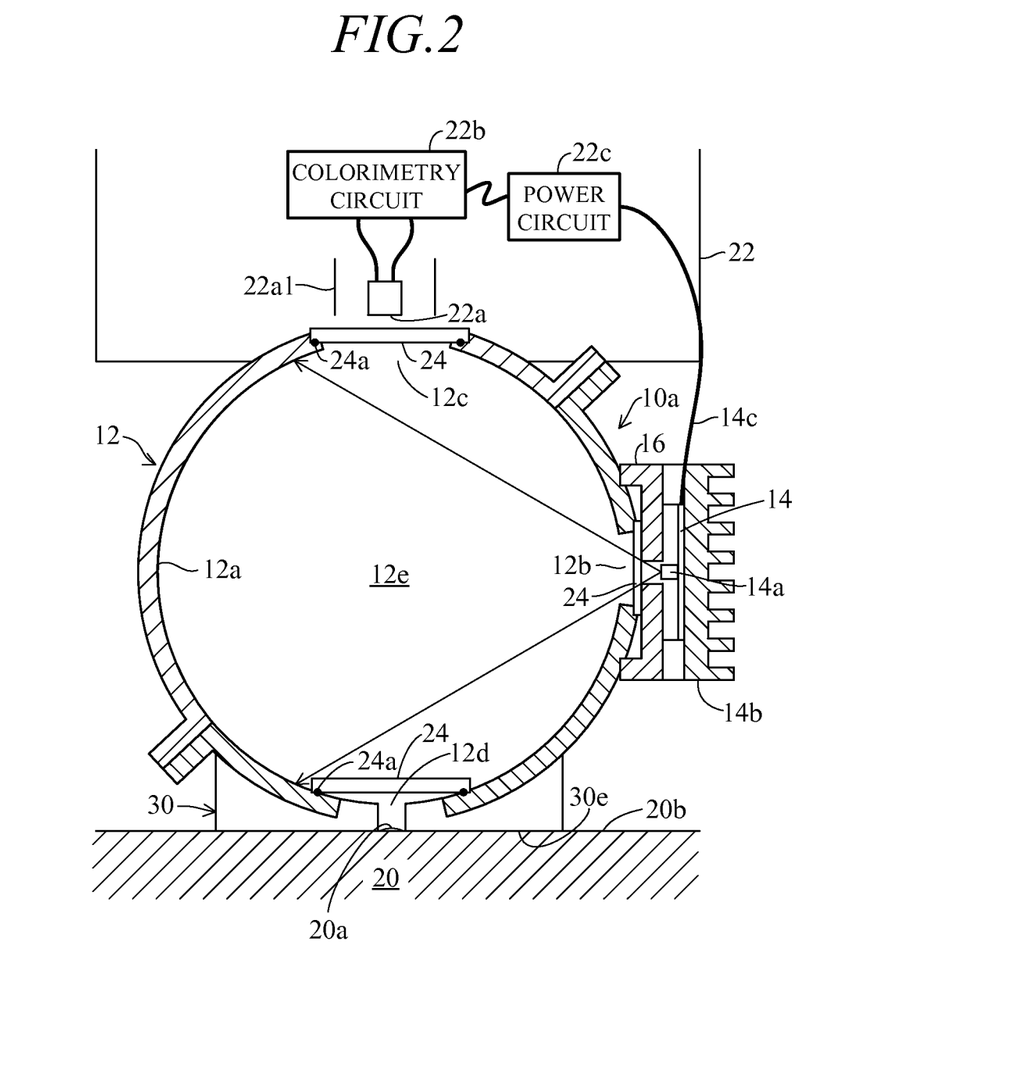
FIG. 2 is an overall schematic view of an integrating sphere according to a second embodiment of this invention.

FIG. 2 is an overall schematic view of the integrating sphere according to the second embodiment of this invention.

The integrating sphere according to the second embodiment, now assigned with symbol 10a, has basically the same structure as that of the integrating sphere 10 according to the first embodiment. Therefore, the second embodiment will be explained with focus on the points of difference from the first embodiment, while marking the same elements with the same symbols and omitting the explanation.

In the integrating sphere 10a according to the second embodiment, the light-emitting device 14a is of a surface-mounting type and, for example in the case of white LED, is made of a blue LED and an yellow illuminant. As shown, the light-emitting device 14a is configured to radiate white light into the spherical space 12e formed with the inner wall 12a of the structure 12 at the input port 12b (more specifically through the input port 12b).

The baffle 16 made of a low thermal conductive material is placed at a location between the LED circuit board 14 and the structure 12. Specifically, LED circuit board 14 is connected to the input port 12 at a location outside of the structure 12 through the baffle 16.

Similarly to the first embodiment, the integrating sphere 10a according to the second embodiment is also equipped, in the vicinity of the measuring port 12d of the structure 12, with the measuring guide 30 that can connect the measuring port 12d to the measuring object 20a (more precisely, the measuring portion of the measuring object 20).

Figure 3:
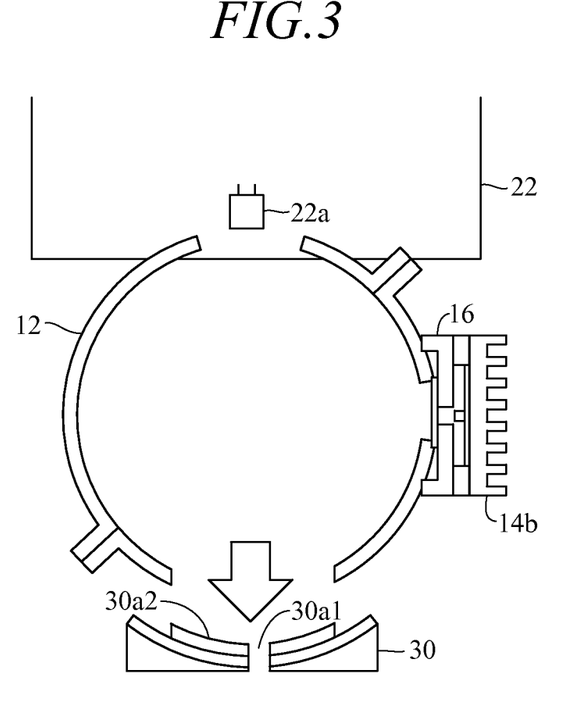
FIG. 3 is an explanatory view showing attachment of a measuring guide to the integrating sphere shown in FIG. 2.
Figure 4:
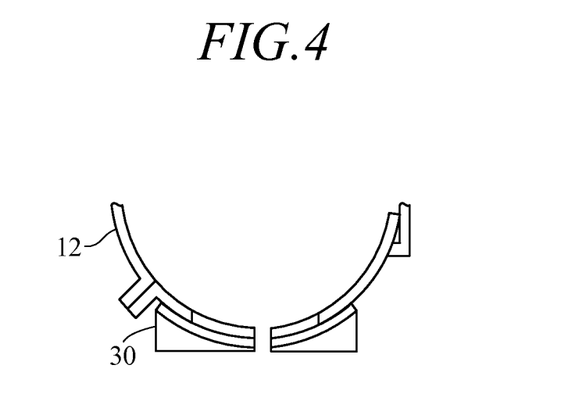
FIG. 4 is an explanatory view similar to FIG. 3 also showing attachment of the measuring guide to the integrating sphere shown in FIG. 2.

As best shown in FIG. 3 and FIG. 4, in the second embodiment (and a fourth embodiment described below), the measuring guide 30 has a covering portion 30a2 that has an external diameter almost the same as an internal diameter of the measuring port 12d of the structure 12 and an enlarged portion that has a larger external diameter than that of the covering portion 30a2. The guide 30 is adapted to be attached to the structure 12 from outside of the measuring port 12d (i.e., outside of the structure 12). The covering portion 30a2 is opened by a center hole 30a1 at its center.

Figure 5:
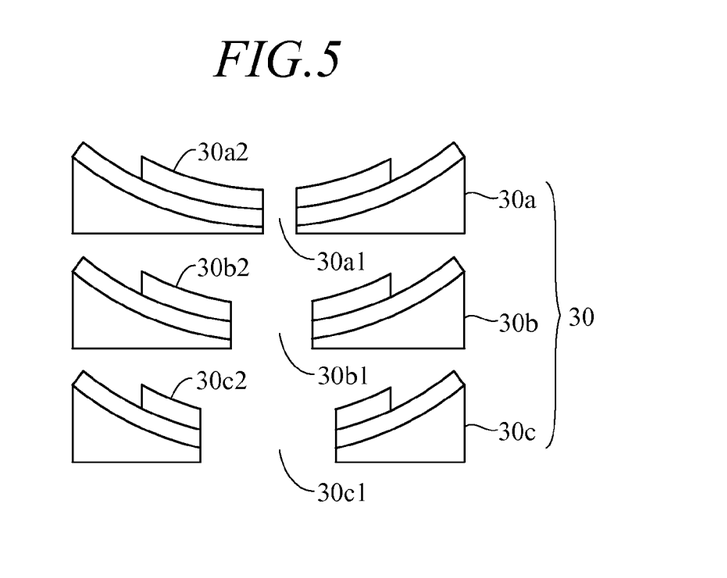
FIG. 5 is an explanatory view showing the measuring guide shown in FIG. 3.
Figure 6:
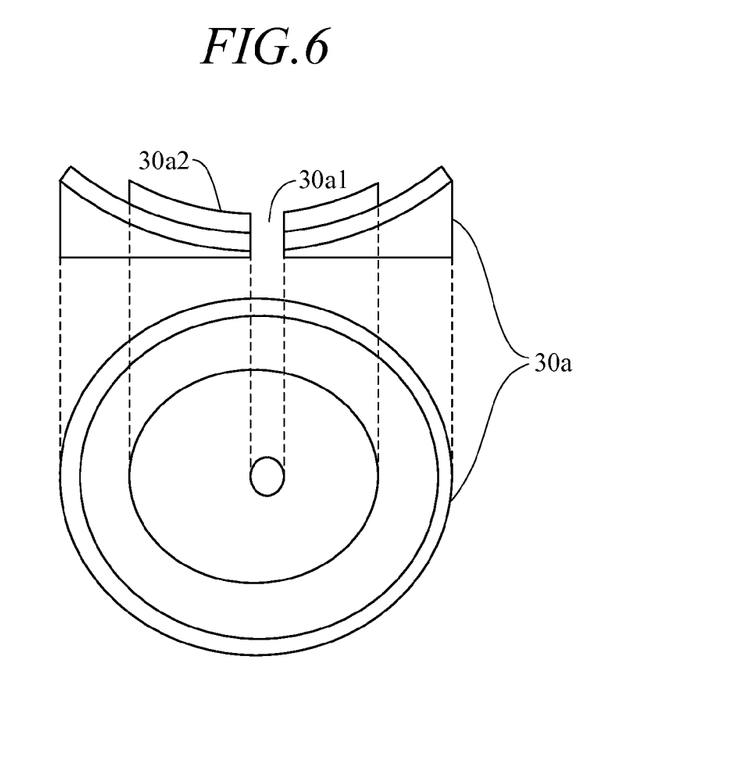
FIG. 6 is an explanatory view similarly showing the measuring guide shown in FIG. 3.

As shown in FIG. 5 and FIG. 6, the measuring guide 30 comprises a plurality of guides, specifically three guides 30a, 30b, 30c. More concretely, the measuring guide 30 comprises the three guides 30a, 30b, 30c each opened by a center hole 30a1, 30b1, 30c1 that has a different diameter.

The covering portions 30a2, 30b2, 30c2 of the measuring guides 30a, 30b, 30c (that face the inner wall 12a of the structure 12) are applied with the same diffuse reflective coating as that of the spherical inner wall 12a of the structure 12, and the surfaces of the covering portions 30a2, 30b2, 30c2 have the same curvature as that of the inner wall 12a of the structure 12.

As mentioned above, in the integrating sphere 10a according to the second embodiment, since the structure 12 of the sphere 10a is also configured to have the measuring port 12d formed at the structure 12 to pass the light diffuse-reflected on the spherical inner wall 12a on the measuring object 20a and the output port 12c formed at the structure 12 to output the reflected light of the diffuse-reflected light passing the measuring port 12d and reflected on the measuring object 20a outside.

With this, it becomes possible to make the diffuse-reflected light of uniform intensity reflect on the measuring object 20a and to measure the color of the measuring object 20a accurately, even when the measuring object 20a is an object that can be affected by an angle at which the measurement is conducted. Further, it becomes possible to eliminate heat generated by the LED circuit board 14 by the heat sink 14b and to prevent heat from diffusing into the structure 12.

Further, since the LED light-emitting device 14a is used as the light source for light radiation, it becomes possible to suppress deterioration of the spherical inner wall 12a, and since the amount of heat generated by the LED light-emitting device 14a is relatively small, it becomes possible to suppress deterioration of the spherical inner wall 12a due to heat emitted from the light-emitting device 14a, thereby enabling to enhance durability.

Since the LED circuit board 14 is placed outside of the structure 12, it becomes possible to suppress deterioration of the spherical inner wall 12a coated with diffuse reflection coating more effectively. Since baffle 16 is placed outside, it becomes possible to prevent lowering of through-put of the computer (colorimetry circuit) 22b.

Since the LED circuit board 14 is connected to the input port 12b at a location outside of the structure 12 through the baffle 16 made of a low thermal conductive material, it becomes possible to further lower heat transfer from the light-emitting device 14a to the spherical inner wall 12a of the structure 12.

Since the integrating sphere is configured such that, the output port 12c and the measuring port 12d are closed with the windows 24 that allow the diffuse-reflected light to pass therethrough, it becomes possible to prevent entry of foreign materials including water or oil vapor into the structure 12, thereby enabling to suppress deterioration or discoloration of the spherical inner wall 12a of the structure 12.

Since the measuring guide 30 adapted to be detachably attached to the structure 12 from outside of the measuring port 12d is included for holding the measuring object 20a on the measurement surface 20b, it becomes possible to position or place the measuring object 20a to the measuring port 12d definitely and easily.

Figure 7A:
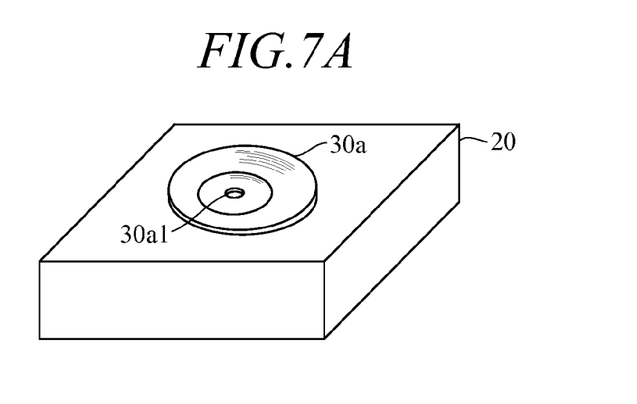
FIGS. 7A-7C are a set of explanatory views schematically showing the procedure for locating the integrating sphere at a position of a measuring object using the measuring guide shown in FIG. 3.
Figure 7B:
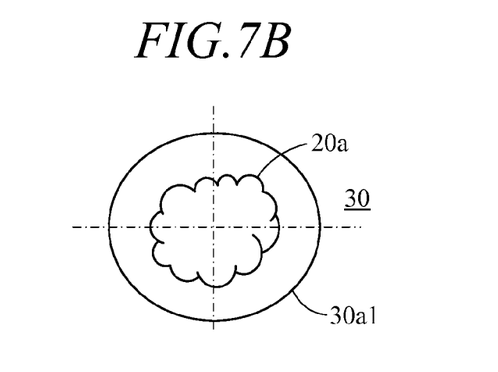
Figure 7C:
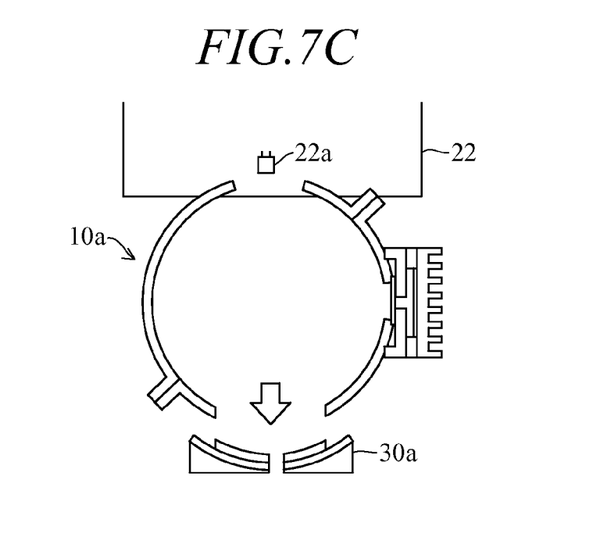

This will be explained in more detail. FIG. 7 is a set of explanatory views schematically showing the procedure of the operator for locating the integrating sphere 10a at a position of the measuring object 20a using the measuring guide 30.

As shown in FIG. 7A, the operator finds the measuring object (portion) 20a on the object 20 visually and places the measuring guide 30 (for example 30a) near the object 20a. Next, as shown in FIG. 7B, he/she moves or adjusts the position of the measuring guide 30a slightly to catch the measuring object 20a concerned in the center hole 30a1. Then, as shown in FIG. 7C, he/she places or positions the integrating sphere 10a on the measuring guide 30a (to attach the measuring guide 30a to the integrating sphere 10a).

Specifically, for example, when the measuring object 20a is a coating color of a vehicle body, it is easy for the operator to position or bring the measuring port 12d to the measuring object 20a. On the contrary, if the measuring object 20a is a local and very small portion of vehicle parts and the like, it is difficult for him/her to locate the measuring position.

If the measuring object 20a is a local and very small portion, but for the measuring guide 30, he/she must move around the integrating sphere 10a repeatedly to catch the measuring object 20a in the measuring port 12d. Since the measuring object 20a can be hidden by the sphere 10a itself when viewed from the above, he/she must view from the side and move the sphere 10a to catch the object 20a in the port 12d, rendering operation incorrect and tedious. However, with the measuring guide 30, it becomes possible to position the integrating sphere 10a on the measuring object 20a precisely and promptly.

The remaining configurations and effects of the sphere 10a according to the second embodiment are the same as those of the first embodiment.

Third Embodiment

Next, an integrating sphere according to a third embodiment of this invention will now be explained with reference to the attached drawings.

Figure 8:
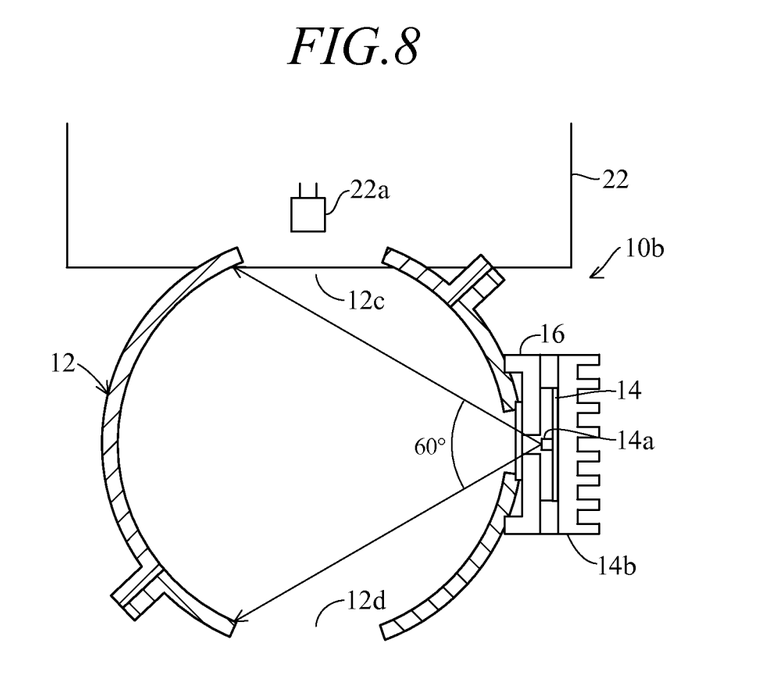
FIG. 8 is an explanatory view partially showing an integrating sphere according to a third embodiment of this invention.

FIG. 8 is an explanatory view partially showing the integrating sphere, now assigned with symbol 10b, according to the third embodiment of this invention.

Explaining the third embodiment with focus on the points of difference from the second embodiment, in the integrating sphere 10b according to the third embodiment, the LED circuit board 14 is configured to have a shell-type light-emitting device 14a similarly to the first embodiment, unlike the light-emitting device 14a of the surface-mounting type of the second embodiment shown in FIG. 2.

Figure 9:
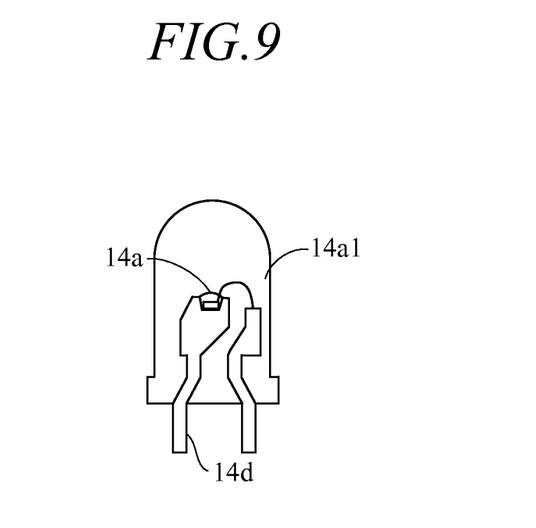
FIG. 9 is an explanatory view showing a shell-type light-emitting device shown in FIG. 8.

More specifically, as shown in FIG. 9, the light-emitting device 14a has a shell like shape sealed with a epoxy resin 14a1 and in the case of white LED, for example, is made of a blue LED and a yellow illuminant, and is configured to radiate white light to the spherical space 12e formed with the inner wall 12a of the structure 12. The light-emitting device 14a has directionality of approximately ±30 degrees.

The LED circuit board 14 is connected to the power circuit 22c through the cable (not shown) and the light-emitting device 14a is connected to the power circuit 22c through a lead 14d (shown in FIG. 9). When supplied with direct current from the power circuit 22c, the LED circuit board 14 activates the light-emitting device 14a to emit the light.

In the third embodiment, the light-emitting device 14a having directionality of ±30 degrees is used as the light source, and as shown in FIG. 8, the device 14 is located at a position in which the angle made by the edge of the output port 12c, the light-emitting device 14a and the edge of the measuring port 12d of the structure 12 is exactly or approximately 60 degrees.

Similarly to the second embodiment, the LED circuit board 14 is also connected to the input port 12b at a location outside of the structure 12 in such a manner that the light radiated from the light-emitting device 14a, more precisely the light outside the 60 degrees is shaded by the baffle 16 made of a low thermal conductive material.

With this, it becomes possible to shade the light outside of the angle range of 60 degrees by the baffle 16 and to achieve lighting more efficiently. The remaining configurations and effects of the sphere 10b according to the third embodiment are the same as those of the first and second embodiments.

Fourth Embodiment

Next, an integrating sphere according to a fourth embodiment of this invention will now be explained with reference to the attached drawings.

Figure 10:
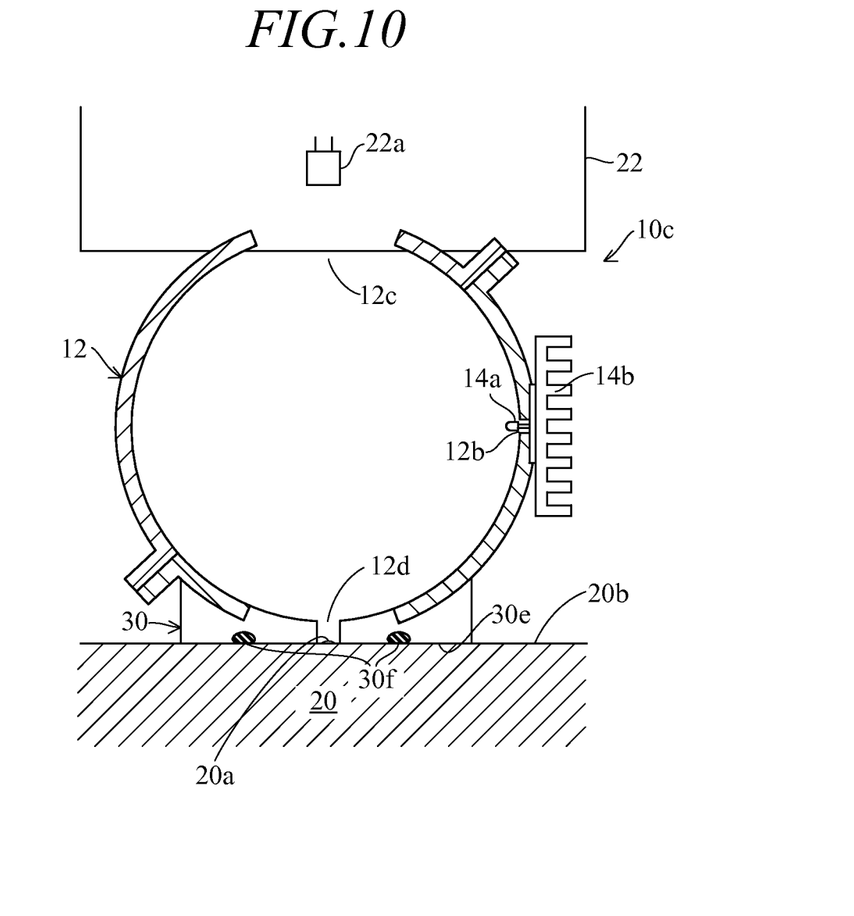
FIG. 10 is an explanatory view partially showing an integrating sphere according to a fourth embodiment of this invention.

FIG. 10 is an explanatory view partially showing the integrating sphere, now assigned with symbol 10c, according to the fourth embodiment of this invention.

Explaining the fourth embodiment with focus on the points of difference from the second embodiment, in the integrating sphere 10c according to the fourth embodiment, the windows 24 for sealing the output port 12c and the measuring port 12d of the structure 12 (referred to in the second embodiment) are removed.

In addition, in the fourth embodiment, the input port 12b is made smaller, i.e., the internal diameter of the input port 12b is made smaller than that of the second embodiment, and the shell-type light-emitting device 14a (similar to that of the third embodiment) is placed at the input port 12b in such a manner that it protrudes into the spherical space 12e through the input port 12b.

In the fourth embodiment, the measuring guide 30 is equipped with a light preventer 30f at the flat surface 30e (that abuts on the measurement surface 20b) for preventing entry of the light into the structure 12 from outside of the integrating sphere 10c through the measuring port 12d.

Having been configured in the foregoing manner, the integrating sphere 10c according to the fourth embodiment is advantageous in that it can make configuration simpler while it degrade sealing property slightly compared to those of the second and third embodiments.

Moreover, since the measuring guide 30 of the integrating sphere 10c according to the fourth embodiment is equipped with the light preventer 30f at its flat surface 30e, it is advantageous in that it can prevent entry of the light into the structure 12 from outside of the integrating sphere 10c through the measuring port 12d and further enhance measurement accuracy.

It should be noted in the fourth embodiment that, although the fourth embodiment is configured to remove the windows 24 from the structure 12 of the second embodiment, it can instead be configured to remove the windows 24 from the structure 12 of the first embodiment.

As stated above, the first to fourth embodiments are configured to have an integrating sphere (10, 10a, 10b, 10c) including a structure (12) having a spherical inner wall (12a) that forms a spherical space (12e), comprising: an LED circuit board (14) equipped at one end with a light-emitting device (14a) adapted to radiate a light in the space (12e) at an input port (12b) formed at the structure (12) to be diffuse-reflected on the spherical inner wall (12a) and equipped at other end with a heat sink (14b); a measuring port (12d) formed at the structure (12) to pass the light diffuse-reflected on the spherical inner wall (12a) on a measuring object (20a); an output port (12c) formed at the structure (12) to output a reflected light of the diffuse-reflected light passing the measuring port (12d) and reflected on the measuring object (20a) outside; and a detector (22) adapted to be detachably connected to the output port (12c) to receive the outputted reflected light. With this, it becomes possible to reduce thermal load on the spherical inner wall (surface) 12a and the measuring object 20a and to suppress deterioration of the spherical inner wall 12a or degradation of measurement accuracy.

Specifically, since it is configured to have the measuring port 12d formed at the structure 12 to pass the light diffuse-reflected on the spherical inner wall 12a on the measuring object 20a and the output port 12c formed at the structure 12 to output a reflected light of the diffuse-reflected light passing the measuring port 12d and reflected on the measuring object 20a outside, it becomes possible to make the diffuse-reflected light of uniform intensity reflect on the measuring object 20a and to measure the color of the measuring object 20a accurately. Even when the measuring object 20a is an object that can be affected by an angle at which the measurement is conducted, it becomes possible to measure its color accurately.

Further, since the LED circuit board 14 is equipped with the heat sink 14b at the other end, it becomes possible to eliminate heat generated by the LED circuit board 14 with the heat sink 14b and to prevent heat from diffusing into the structure 12.

Further, since the LED light-emitting device 14a is used as the light source for light radiation, it becomes possible to select a region of wavelength to be radiated appropriately to suppress infrared radiation and hence, it becomes possible to prevent overheating of the measuring object 20a due to infrared light, thereby enabling to measure the measuring object 20a without discoloring it.

Furthermore, since the structure 12 has the spherical inner wall (surface) 12a coated with diffuse reflective coating inside and is able to eliminate the light in a specific wavelength region such as infrared light and ultraviolet light that accelerates deterioration of diffuse reflective coating, it becomes possible to suppress deterioration of the spherical inner wall 12a. In addition, since the amount of heat generated by the LED light-emitting device 14a is relatively small, it becomes possible to suppress deterioration of the spherical inner wall 12a due to heat emitted from the light-emitting device 14a, thereby enabling to enhance durability.

The integrating sphere is configured such that, the input port (12b), the output port (12c) and the measuring port (12d) are formed in the spherical space (12e) in such a manner that a crossing angle (θ1) of a central axis line (12b2) of the input port (12b) and a central axis line (12c1) of the output port (12c) is 90 degrees and a crossing angle (θ2) of the central axis line (12c1) of the output port (12c) and a normal line (12d1) extending from a measuring surface (20b) on which the measuring object (20a) is held towards the spherical space (12e) through a center of the measuring port (12d) is an angle within a predetermined range. With this, in addition to the aforesaid advantages and effects, it becomes possible to make the fabrication of the structure 12 easier.

Specifically, the structure 12 needs to be formed fixing portions for fixing or attaching the LED circuit board 14 (or light-emitting device 14a) or the detector 22 at the input port 12b and output port 12c and it is inherently tedious to fabricate them. However, since the crossing angle θ1 of the central axis line 12b2 of the input port 12b and the central axis line 12c1 of the output port 12c is made 90 degrees, i.e., is made exactly or absolutely 90 degrees, it becomes possible to simplify the configuration of the structure 12 and to facilitate the fabrication.

In addition, since the crossing angle θ2 of the central axis line 12c1 of the output port 12c and the normal line 12d1 extending from a measuring surface 20b on which the measuring object 20a is held towards the spherical space 12e through the center of the measuring port 12d is made an angle within a predetermined range, for example an angle greater than 0 degree and equal to or smaller than 10 degrees, it becomes possible to prevent the light reflected from the measuring object 20a from entering the detector 22 at a regular reflection angle (angle at which the reflection angle becomes equal to the incident angle), thereby enabling to enhance measurement accuracy.

Further, since the crossing angle θ2 of the central axis line 12c1 of the output port 12c and the normal line 12d1 extending from a measuring surface 20b (on which the measuring object 20a is held) towards the spherical space 12e through the center of the measuring port 12d is made an angle within a predetermined range, it becomes possible to make the size of the baffle 16 (for preventing direct incident from the light-emitting device 14a to the measuring object 20a) smaller.

The integrating sphere is configured such that, the input port (12b), the measuring port (12d) is formed at the structure (12) in such a manner that the normal line (12d1) extends through a center point (12e1) of the spherical space (12e). With this, in addition to the aforesaid advantages and effects, it becomes possible to allow the light radiated from the light-emitting device 14a and diffuse-reflected on the spherical inner wall 12a to uniformly enter to be reflected on the measuring object 20a, thereby enabling to enhance measurement accuracy.

The integrating sphere is configured such that, the detector (22) is detachably attached to the output port (12c) through a duct (22a1). With this, in addition to the aforesaid advantages and effects, it becomes possible to effectively prevent the light incident from other than the measuring object 20a, thereby enabling to enhance measurement accuracy.

The integrating sphere is configured such that, the LED circuit board (14) is placed outside of the structure (12) in such a manner that the light radiated from the light-emitting device enters the space (12e) through the input port (12b). With this, in addition to the aforesaid advantages and effects, since the light source is not placed inside of the structure 12, it becomes possible to suppress deterioration of the spherical inner wall 12a coated with diffuse reflection coating more effectively.

The integrating sphere is configured such that, the LED circuit board (14) is connected to the input port (12b) at a location outside of the structure (12) through a baffle (16) made of a low thermal conductive material. With this, in addition to the aforesaid advantages and effects, it becomes possible to lower heat transfer from the light-emitting device 14a to the spherical inner wall 12a more effectively. In addition, since the baffle 16 needs not be placed inside of the structure 12, it becomes possible to prevent throughput decrease which would otherwise be occurred if the baffle 16 is placed inside.

The integrating sphere is configured such that, the output port (12c) and the measuring port (12d) are closed with windows (24) that allow the diffuse-reflected light to pass therethrough. With this, in addition to the aforesaid advantages and effects, it becomes possible to prevent entry of foreign materials including water or oil vapor into the structure 12, thereby enabling to suppress deterioration or discoloration of the spherical inner wall 12a.

The integrating sphere is configured such that, it further includes: a measuring guide (30) adapted to be detachably attached to the structure from outside of the measuring port (12d) for holding the measuring object (20a) on a measurement surface (20b). With this, in addition to the aforesaid advantages and effects, it becomes possible to position the measuring object 20a to the measuring port 12d definitely and by the measuring guide 30, it becomes possible to position the measuring port 12d to the measuring object 20a easily.

Specifically, for example, when the measuring object 20a is a coating color of a vehicle body, it is easy for the operator to position or bring the measuring port 12d to the measuring object 20a. On the contrary, if the measuring object 20a is a local and very small portion of vehicle parts and the like, it is difficult for the operator to locate the measuring position and bring the measuring port 12d there promptly.

However, with the measuring guide 30, it becomes possible for the operator to take the measuring guide 30 out of the structure 12, look for the measuring object 20a, position the measuring guide 30 there, and place the structure 12 to the measuring guide 30, thereby enabling to position the measuring port 12d to the measuring object 20a easily and promptly.

The integrating sphere is configured such that, the measuring guide (30) comprises a plurality of guides (30a, 30b, 30c) each opened by a hole (30a1, 30b1, 30c1) having a different diameter. With this, in addition to the aforesaid advantages and effects, it becomes possible to select the measuring guide 30 of a suitable hole diameter in accordance with the measuring object 20a, thereby enabling to enhance measurement accuracy.

The integrating sphere is configured such that, the measuring guide (30) is applied with a same diffuse reflective coating as that of the spherical inner wall (12a) on a surface facing the spherical inner wall (12a). With this, in addition to the aforesaid advantages and effects, it becomes possible to make the light of a uniform intensity obtained by diffuse reflection like the inner wall 12a reflect on the measuring object 20a, thereby enabling to enhance measurement accuracy.

The integrating sphere is configured such that, the surface of the measuring guide (30) facing the spherical inner wall (12a) has a same curvature as that of the spherical inner wall (12a) of the structure (12). With this, in addition to the aforesaid advantages and effects, it becomes possible to make the light of a uniform intensity obtained by diffuse reflection like the inner wall 12a reflect on the measuring object 20a, thereby enabling to enhance measurement accuracy.

The integrating sphere is configured such that, the measuring guide (30) is equipped with a light preventer (30f) at a flat surface (30e) abutting on the measurement surface (20b). With this, in addition to the aforesaid advantages and effects, it becomes possible to prevent entry of the light from outside of the integrating sphere 10c through the measuring port 12d into the structure 12, thereby enabling to further enhance measurement accuracy.

It should be noted that, although the light-emitting device 14a is configured to use a white LED as above, any configuration that can radiate light in target measurement wavelength region without generating infrared or ultraviolet light, can instead be used.

It should further be noted that, although the configuration of the integrating sphere is described taking color analysis of the measuring object as an example, the configuration of the integrating sphere according to this invention can be for integrating spheres used for various purposes such as measurement of luminous flux of the light source.

It should further be noted that, although the configuration of the integrating sphere coated with diffuse reflective coating is described as an example, any configuration that has high reflectivity in target measurement wavelength region, such as a configuration integrally molded with barium-containing plastic, can instead be used.

Japanese Patent Application Nos. 2013-120693, filed on Jun. 7, 2013, and 2014-049969, filed on Mar. 13, 2014, are incorporated by reference herein in its entirety.

While the invention has thus been shown and described with reference to specific embodiments, it should be noted that the invention is in no way limited to the details of the described arrangements; changes and modifications may be made without departing from the scope of the appended claims.

What is claimed is:

1. An integrating sphere, comprising:
a structure having a spherical inner wall that forms a spherical space;
an LED circuit board equipped at one end with a light-emitting device configured to radiate a light in the space at an input port formed at the structure to be diffuse-reflected on the spherical inner wall and equipped at other end with a heat sink;
a measuring port formed at the structure to pass the light diffuse-reflected on the spherical inner wall on a measured object on a measurement surface;
an output port formed at the structure to output a reflected light of the diffuse-reflected light passing the measuring port and reflected on the measured object outside;
a detector configured to be detachably connected to the output port to receive the outputted reflected light; and
a measuring guide configured to be detachably attachable to the structure from outside of the measuring port for positioning the integrating sphere on the measured object on the measurement surface, the measuring guide having a center hole configured to allow an operator to visually position the measuring guide on the measured object on the measurement surface, the center hole being configured to pass light from the measuring port to the measured object and to pass light reflected off the measured object to the measuring port,
wherein the measuring guide comprises a covering portion configured to position the integrating sphere so that the output port is placed opposite to the center hole, and
wherein the covering portion is configured to fit inside the measuring port of the integrating sphere.

2. The integrating sphere according to claim 1, wherein the input port, the output port and the measuring port are formed in the spherical space in such a manner that a crossing angle of a central axis line of the input port and a central axis line of the output port is 90 degrees and a crossing angle of the central axis line of the output port and a normal line extending from a measuring surface on which the measured object is held towards the spherical space through a center of the measuring port is an angle within a predetermined range.

3. The integrating sphere according to claim 2, wherein the measuring port is formed at the structure in such a manner that the normal line extends through a center point of the spherical space.

4. The integrating sphere according to claim 1, wherein the detector is detachably attached to the output port through a duct.

5. The integrating sphere according to claim 1, wherein the LED circuit board is placed outside of the structure in such a manner that the light radiated from the light-emitting device enters the space through the input port.

6. The integrating sphere according to claim 1, wherein the LED circuit board is connected to the input port at location outside of the structure through a baffle made of a low thermal conductivity material.

7. The integrating sphere according to claim 1, wherein the output port and the measuring port are closed with windows that allow the diffuse-reflected light to pass therethrough.

8. The integrating sphere according to claim 1, wherein the measuring guide comprises a plurality of guides each opened by a hole having a different diameter.

9. The integrating sphere according to claim 1, wherein the measuring guide is applied with a same diffuse reflective coating as that of the spherical inner wall on a surface facing the spherical inner wall.

10. The integrating sphere according to claim 9, wherein the surface of the measuring guide facing the spherical inner wall has a same curvature as that of the spherical inner wall of the structure.

11. The integrating sphere according to claim 1, wherein the measuring guide is equipped with a light preventer at a flat surface abutting on the measurement surface.

* * * * *